(12) United States Patent
Yun et al.

(10) Patent No.: US 10,656,105 B2
(45) Date of Patent: May 19, 2020

(54) TALBOT-LAU X-RAY SOURCE AND INTERFEROMETRIC SYSTEM

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US); David Vine, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 0 days.

(21) Appl. No.: 16/525,198

(22) Filed: Jul. 29, 2019

(65) Prior Publication Data

US 2020/0041428 A1 Feb. 6, 2020

Related U.S. Application Data

(60) Provisional application No. 62/715,164, filed on Aug. 6, 2018.

(51) Int. Cl.
*G01N 23/20* (2018.01)
*G01N 23/02* (2006.01)
(Continued)

(52) U.S. Cl.
CPC ....... *G01N 23/20075* (2013.01); *G01N 23/02* (2013.01); *A61B 6/032* (2013.01); *A61B 6/4291* (2013.01); *G01N 2223/204* (2013.01)

(58) Field of Classification Search
None
See application file for complete search history.

(56) References Cited

U.S. PATENT DOCUMENTS

| 1,203,495 A | 10/1916 | Coolidge |
| 1,211,092 A | 1/1917 | Coolidge |

(Continued)

FOREIGN PATENT DOCUMENTS

| CN | 101257851 | 9/2008 |
| CN | 101532969 | 9/2009 |

(Continued)

OTHER PUBLICATIONS

Behling, "Medical X-ray sources Now and for the Future," Nucl. Inst. and Methods in Physics Research A 873, pp. 43-50 (2017).

(Continued)

*Primary Examiner* — Hoon K Song
(74) *Attorney, Agent, or Firm* — Knobbe, Martens Olson & Bear LLP

(57) ABSTRACT

An x-ray source and an x-ray interferometry system utilizing the x-ray source are provided. The x-ray source includes a target that includes a substrate and a plurality of structures. The substrate includes a thermally conductive first material and a first surface. The plurality of structures is on or embedded in at least a portion of the first surface. The structures are separate from one another and are in thermal communication with the substrate. The structures include at least one second material different from the first material, the at least one second material configured to generate x-rays upon irradiation by electrons having energies in an energy range of 0.5 keV to 160 keV. The x-ray source further includes an electron source configured to generate the electrons and to direct the electrons to impinge the target and to irradiate at least some of the structures along a direction that is at a non-zero angle relative to a surface normal of the portion of the first surface. The x-ray source further includes at least one optical element positioned such that at least (Continued)

some of the x-rays are transmitted through the first material and to or through the at least one optical element.

28 Claims, 6 Drawing Sheets

(51) Int. Cl.
A61B 6/00 (2006.01)
A61B 6/03 (2006.01)

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,165,472 A | 8/1979 | Wittry |
| 4,227,112 A | 10/1980 | Waugh et al. |
| 4,266,138 A | 5/1981 | Nelson et al. |
| 4,426,718 A | 1/1984 | Hayashi |
| 4,523,327 A | 6/1985 | Eversole |
| 4,573,186 A | 2/1986 | Reinhold |
| 4,807,268 A | 2/1989 | Wittry |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,119,408 A | 6/1992 | Little |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,513,237 A | 4/1996 | Nobuta et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,737,387 A | 4/1998 | Smither |
| 5,768,339 A | 6/1998 | O'Hara |
| 5,772,903 A | 6/1998 | Hirsch |
| 5,778,039 A | 7/1998 | Hossain |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,118,853 A | 9/2000 | Hansen et al. |
| 6,125,167 A | 9/2000 | Morgan |
| 6,278,764 B1 | 8/2001 | Barbee, Jr. et al. |
| 6,307,916 B1 | 10/2001 | Rogers et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,430,260 B1 | 8/2002 | Snyder |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,763,086 B2 | 7/2004 | Platonov |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,891,627 B1 | 5/2005 | Levy et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1 | 2/2006 | Janik |
| 7,015,467 B2 | 3/2006 | Maldonado et al. |
| 7,023,950 B1 | 4/2006 | Annis |
| 7,023,955 B2 | 4/2006 | Chen et al. |
| 7,057,187 B1 | 6/2006 | Yun et al. |
| 7,076,026 B2 | 6/2006 | Verman et al. |
| 7,079,625 B2 | 7/2006 | Lenz |
| 7,095,822 B1 | 8/2006 | Yun |
| 7,103,138 B2 | 9/2006 | Pelc et al. |
| 7,110,503 B1 | 9/2006 | Kumakhov |
| 7,119,953 B2 | 10/2006 | Yun et al. |
| 7,120,228 B2 | 10/2006 | Yokhin et al. |
| 7,130,375 B1 | 10/2006 | Yun et al. |
| 7,170,969 B1 | 1/2007 | Yun et al. |
| 7,180,979 B2 | 2/2007 | Momose |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,264,397 B2 | 9/2007 | Ritter |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,349,525 B2 | 3/2008 | Morton |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,440,542 B2 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,515,684 B2 | 4/2009 | Gibson et al. |
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |

(56) References Cited

U.S. PATENT DOCUMENTS

| | | |
|---|---|---|
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |
| 7,605,371 B2 | 10/2009 | Yasui et al. |
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,738,629 B2 | 6/2010 | Chen |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,809,113 B2 | 10/2010 | Aoki et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,864,922 B2 | 1/2011 | Kawabe |
| 7,873,146 B2 | 1/2011 | Okunuki et al. |
| 7,876,883 B2 | 1/2011 | O'Hara |
| 7,889,838 B2 | 2/2011 | David et al. |
| 7,889,844 B2 | 2/2011 | Okunuki et al. |
| 7,899,154 B2 | 3/2011 | Chen et al. |
| 7,902,528 B2 | 3/2011 | Hara et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,009,797 B2 | 8/2011 | Ouchi |
| 8,041,004 B2 | 10/2011 | David |
| 8,036,341 B2 | 11/2011 | Lee |
| 8,058,621 B2 | 11/2011 | Kommareddy |
| 8,068,579 B1 | 11/2011 | Yun et al. |
| 8,073,099 B2 | 12/2011 | Niu et al. |
| 8,094,784 B2 | 1/2012 | Morton |
| 8,139,711 B2 | 3/2012 | Takahashi |
| 8,139,716 B2 | 3/2012 | Okunuki et al. |
| 8,184,771 B2 | 5/2012 | Murakoshi |
| 8,208,602 B2 | 6/2012 | Lee |
| 8,208,603 B2 | 6/2012 | Sato |
| 8,233,587 B2 | 7/2012 | Sato |
| 8,243,879 B2 | 8/2012 | Itoh et al. |
| 8,243,884 B2 | 8/2012 | Rödhammer et al. |
| 8,249,220 B2 | 8/2012 | Verman et al. |
| 8,280,000 B2 | 10/2012 | Takahashi |
| 8,306,183 B2 | 11/2012 | Koehler |
| 8,306,184 B2 | 11/2012 | Chang et al. |
| 8,331,534 B2 | 12/2012 | Silver |
| 8,351,569 B2 | 1/2013 | Baker |
| 8,351,570 B2 | 1/2013 | Nakamura |
| 8,353,628 B1 | 1/2013 | Yun et al. |
| 8,357,894 B2 | 1/2013 | Toth et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,594 B2 | 10/2013 | Ouchi |
| 8,559,597 B2 | 10/2013 | Chen et al. |
| 8,565,371 B2 | 10/2013 | Bredno |
| 8,576,983 B2 | 11/2013 | Baeumer |
| 8,588,372 B2 | 11/2013 | Zou et al. |
| 8,591,108 B2 | 11/2013 | Tada |
| 8,602,648 B1 | 12/2013 | Jacobsen et al. |
| 8,632,247 B2 | 1/2014 | Ishii |
| 8,644,451 B2 | 2/2014 | Aoki et al. |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,859,977 B2 | 10/2014 | Kondoh |
| 8,861,682 B2 | 10/2014 | Okunuki et al. |
| 8,903,042 B2 | 12/2014 | Ishii |
| 8,908,824 B2 | 12/2014 | Kondoh |
| 8,972,191 B2 | 3/2015 | Stampanoni et al. |
| 8,989,351 B2 | 3/2015 | Vogtmeier et al. |
| 8,989,474 B2 | 3/2015 | Kido et al. |
| 8,995,622 B2 | 3/2015 | Adler et al. |
| 9,001,967 B2 | 4/2015 | Baturin |
| 9,001,968 B2 | 4/2015 | Kugland et al. |
| 9,007,562 B2 | 4/2015 | Marconi et al. |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,025,725 B2 | 5/2015 | Kiyohara et al. |
| 9,031,201 B2 | 5/2015 | Sato |
| 9,063,055 B2 | 6/2015 | Ouchi |
| 9,086,536 B2 | 7/2015 | Pang et al. |
| 9,129,715 B2 | 9/2015 | Adler et al. |
| 9,222,899 B2 | 12/2015 | Yamaguchi |
| 9,257,254 B2 | 2/2016 | Ogura et al. |
| 9,263,225 B2 | 2/2016 | Morton |
| 9,280,056 B2 | 3/2016 | Clube et al. |
| 9,291,578 B2 | 3/2016 | Adler |
| 9,329,141 B2 | 5/2016 | Stutman |
| 9,336,917 B2 | 5/2016 | Ozawa et al. |
| 9,357,975 B2 | 6/2016 | Baturin |
| 9,362,081 B2 | 6/2016 | Bleuet |
| 9,370,084 B2 | 6/2016 | Sprong et al. |
| 9,390,881 B2 | 7/2016 | Yun et al. |
| 9,412,552 B2 | 8/2016 | Aoki et al. |
| 9,430,832 B2 | 8/2016 | Koehler et al. |
| 9,439,613 B2 | 9/2016 | Stutman |
| 9,445,775 B2 | 9/2016 | Das |
| 9,448,190 B2 | 9/2016 | Yun et al. |
| 9,449,780 B2 | 9/2016 | Chen |
| 9,449,781 B2 | 9/2016 | Yun et al. |
| 9,453,803 B2 | 9/2016 | Radicke |
| 9,486,175 B2 | 11/2016 | Fredenberg et al. |
| 9,494,534 B2 | 11/2016 | Baturin |
| 9,520,260 B2 | 12/2016 | Hesselink et al. |
| 9,524,846 B2 | 12/2016 | Sato et al. |
| 9,532,760 B2 | 1/2017 | Anton et al. |
| 9,543,109 B2 | 1/2017 | Yun et al. |
| 9,564,284 B2 | 2/2017 | Gerzoskovitz |
| 9,570,264 B2 | 2/2017 | Ogura et al. |
| 9,570,265 B1 | 2/2017 | Yun et al. |
| 9,588,066 B2 | 3/2017 | Pois et al. |
| 9,594,036 B2 | 3/2017 | Yun et al. |
| 9,632,040 B2 | 4/2017 | Stutman |
| 9,700,267 B2 | 7/2017 | Baturin et al. |
| 9,719,947 B2 | 8/2017 | Yun et al. |
| 9,748,012 B2 | 8/2017 | Yokoyama |
| 9,757,081 B2 | 9/2017 | Proksa |

(56) References Cited

U.S. PATENT DOCUMENTS

| | | |
|---|---|---|
| 9,761,021 B2 | 9/2017 | Koehler |
| 9,823,203 B2 | 11/2017 | Yun et al. |
| 9,826,949 B2 | 11/2017 | Ning |
| 9,837,178 B2 | 12/2017 | Nagai |
| 9,842,414 B2 | 12/2017 | Koehler |
| 9,861,330 B2 | 1/2018 | Rossl |
| 9,874,531 B2 | 1/2018 | Yun et al. |
| 9,881,710 B2 | 1/2018 | Roessl |
| 9,916,655 B2 | 3/2018 | Sampanoni |
| 9,934,930 B2 | 4/2018 | Parker et al. |
| 9,939,392 B2 | 4/2018 | Wen |
| 9,970,119 B2 | 5/2018 | Yokoyama |
| 10,014,148 B2 | 7/2018 | Tang et al. |
| 10,028,716 B2 | 7/2018 | Rossl |
| 10,045,753 B2 | 8/2018 | Teshima et al. |
| 10,068,740 B2 | 9/2018 | Gupta |
| 10,074,451 B2 | 9/2018 | Kottler et al. |
| 10,076,297 B2 | 9/2018 | Bauer |
| 10,085,701 B2 | 10/2018 | Hoshino |
| 10,141,081 B2 | 11/2018 | Preusche |
| 10,151,713 B2 | 12/2018 | Wu et al. |
| 10,153,061 B2 | 12/2018 | Yokoyama |
| 10,153,062 B2 | 12/2018 | Gall et al. |
| 10,182,194 B2 | 1/2019 | Karim et al. |
| 10,217,596 B2 | 2/2019 | Liang et al. |
| 10,231,687 B2 | 3/2019 | Kahn et al. |
| 10,247,683 B2 | 4/2019 | Yun et al. |
| 10,256,001 B2 | 4/2019 | Yokoyama |
| 10,264,659 B1 | 4/2019 | Miller et al. |
| 10,267,752 B2 | 4/2019 | Zhang et al. |
| 10,267,753 B2 | 4/2019 | Zhang et al. |
| 10,269,528 B2 | 4/2019 | Yun et al. |
| 10,295,485 B2 | 5/2019 | Yun et al. |
| 10,295,486 B2 | 5/2019 | Yun et al. |
| 10,297,359 B2 | 5/2019 | Yun et al. |
| 10,304,580 B2 | 5/2019 | Yun et al. |
| 10,349,908 B2 | 7/2019 | Yun et al. |
| 10,352,695 B2 | 7/2019 | Dziura et al. |
| 10,352,880 B2 | 7/2019 | Yun et al. |
| 10,393,683 B2 | 8/2019 | Hegeman et al. |
| 10,401,309 B2 | 9/2019 | Yun et al. |
| 10,416,099 B2 | 9/2019 | Yun et al. |
| 10,429,325 B2 | 10/2019 | Ito et al. |
| 2001/0006413 A1 | 7/2001 | Burghoorn |
| 2002/0085676 A1 | 7/2002 | Snyder |
| 2003/0142790 A1 | 1/2003 | Zhou et al. |
| 2003/0223536 A1 | 12/2003 | Yun et al. |
| 2004/0047446 A1 | 3/2004 | Platonov |
| 2004/0120463 A1 | 6/2004 | Wilson et al. |
| 2004/0140432 A1 | 7/2004 | Maldonado et al. |
| 2005/0025281 A1 | 2/2005 | Verman et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1 | 3/2006 | Pelc |
| 2006/0062350 A1 | 3/2006 | Yokhin |
| 2006/0233309 A1 | 10/2006 | Kutzner et al. |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0116398 A1 | 5/2008 | Hara |
| 2008/0117511 A1 | 5/2008 | Chen |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1 | 2/2009 | Endoh |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0046702 A1 | 2/2010 | Chen et al. |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0235976 A1 | 9/2013 | Jeong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0071402 A1 | 3/2015 | Handa |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |

(56) References Cited

U.S. PATENT DOCUMENTS

| | | | |
|---|---|---|---|
| 2015/0247811 A1 | 9/2015 | Yun et al. | |
| 2015/0260663 A1 | 9/2015 | Yun et al. | |
| 2015/0323478 A1 | 11/2015 | Stutman | |
| 2015/0357069 A1* | 12/2015 | Yun | G01N 23/2076 378/44 |
| 2016/0064175 A1 | 3/2016 | Yun et al. | |
| 2016/0066870 A1* | 3/2016 | Yun | A61B 6/4035 378/21 |
| 2016/0106387 A1 | 4/2016 | Kahn | |
| 2016/0178540 A1 | 6/2016 | Yun et al. | |
| 2016/0268094 A1 | 9/2016 | Yun et al. | |
| 2016/0320320 A1 | 11/2016 | Yun et al. | |
| 2016/0351370 A1 | 12/2016 | Yun et al. | |
| 2017/0018392 A1 | 1/2017 | Cheng | |
| 2017/0047191 A1 | 2/2017 | Yun et al. | |
| 2017/0052128 A1 | 2/2017 | Yun et al. | |
| 2017/0162288 A1 | 6/2017 | Yun et al. | |
| 2017/0162359 A1 | 6/2017 | Tang et al. | |
| 2017/0227476 A1 | 8/2017 | Zhang et al. | |
| 2017/0234811 A1 | 8/2017 | Zhang et al. | |
| 2017/0261442 A1 | 9/2017 | Yun et al. | |
| 2017/0336334 A1 | 11/2017 | Yun et al. | |
| 2018/0144901 A1* | 5/2018 | Yun | H01J 35/105 |
| 2018/0261352 A1 | 9/2018 | Matsuyama et al. | |
| 2018/0306734 A1 | 10/2018 | Morimoto et al. | |
| 2018/0323032 A1 | 11/2018 | Strelec et al. | |
| 2018/0344276 A1 | 12/2018 | DeFreitas et al. | |
| 2018/0348151 A1 | 12/2018 | Kasper et al. | |
| 2018/0356355 A1 | 12/2018 | Momose et al. | |
| 2019/0017942 A1 | 1/2019 | Filevich | |
| 2019/0017946 A1 | 1/2019 | Wack et al. | |
| 2019/0018824 A1 | 1/2019 | Zarkadas | |
| 2019/0019647 A1 | 1/2019 | Lee et al. | |
| 2019/0027265 A1 | 1/2019 | Dey et al. | |
| 2019/0043689 A1 | 2/2019 | Camus | |
| 2019/0057832 A1 | 2/2019 | Durst et al. | |
| 2019/0064084 A1 | 2/2019 | Ullom et al. | |
| 2019/0086342 A1 | 3/2019 | Pois et al. | |
| 2019/0088439 A1 | 3/2019 | Honda | |
| 2019/0113466 A1 | 4/2019 | Karim et al. | |
| 2019/0115184 A1 | 4/2019 | Zalubovsky | |
| 2019/0131103 A1 | 5/2019 | Tuohimaa | |
| 2019/0132936 A1 | 5/2019 | Steck et al. | |
| 2019/0154892 A1 | 5/2019 | Moldovan | |
| 2019/0172681 A1 | 6/2019 | Owen et al. | |
| 2019/0189385 A1 | 6/2019 | Liang et al. | |
| 2019/0204246 A1 | 7/2019 | Hegeman et al. | |
| 2019/0204757 A1 | 7/2019 | Brussard et al. | |
| 2019/0206652 A1 | 7/2019 | Akinwande et al. | |
| 2019/0214216 A1 | 7/2019 | Jeong et al. | |
| 2019/0216416 A1 | 7/2019 | Koehler et al. | |
| 2019/0219713 A1 | 7/2019 | Booker et al. | |
| 2019/0261935 A1 | 8/2019 | Kitamura | |
| 2019/0272929 A1 | 9/2019 | Omote et al. | |
| 2019/0304735 A1 | 10/2019 | Safai et al. | |
| 2019/0311874 A1 | 10/2019 | Tuohimnna et al. | |
| 2019/0317027 A1 | 10/2019 | Tsuboi et al. | |
| 2019/0341219 A1 | 11/2019 | Zhang et al. | |
| 2019/0341220 A1 | 11/2019 | Parker et al. | |
| 2019/0353802 A1 | 11/2019 | Steinhauser et al. | |
| 2019/0374182 A1 | 12/2019 | Karim et al. | |
| 2019/0380193 A1 | 12/2019 | Matsuhana et al. | |
| 2019/0387602 A1 | 12/2019 | Woywode et al. | |
| 2019/0391087 A1 | 12/2019 | Matejka et al. | |
| 2020/0003708 A1 | 1/2020 | Kobayashi et al. | |
| 2020/0003712 A1 | 1/2020 | Kataoka et al. | |

FOREIGN PATENT DOCUMENTS

| | | |
|---|---|---|
| CN | 102124537 A | 7/2011 |
| CN | 102325498 | 1/2012 |
| CN | 102551761 A | 7/2012 |
| EP | 0432568 | 6/1991 |
| EP | 0751533 | 1/1997 |
| EP | 1028451 | 8/2000 |
| EP | 1169713 | 1/2006 |
| FR | 2548447 | 1/1985 |
| JP | H06-188092 | 7/1994 |
| JP | H07-056000 | 3/1995 |
| JP | H08-184572 | 7/1996 |
| JP | H11-304728 | 11/1999 |
| JP | 2000-306533 | 11/2000 |
| JP | 2003-149392 | 5/2003 |
| JP | 2003-288853 | 10/2003 |
| JP | 2004-089445 | 3/2004 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-145111 | 6/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-032387 | 2/2012 |
| JP | 2012-187341 | 10/2012 |
| JP | 2012-254294 | 12/2012 |
| JP | 2013-508683 | 3/2013 |
| JP | 2013-157269 | 8/2013 |
| JP | 2013-160637 | 8/2013 |
| JP | 2013-181811 | 9/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO 1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/125833 | 11/2007 |
| WO | WO 2009/098027 | 8/2009 |
| WO | WO 2009/1104560 | 8/2009 |
| WO | WO 2010/109909 | 9/2010 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

Chang et al., "Ultra-high aspect ratio high-resolution nanofabrication of hard X-ray diffractive optics," Nature Comm. 5:4243, doi: 10.1038/ncomms5243 (2014).

Dittler et al., "A mail-in and user facility for X-ray absorption near-edge structure: the CEI-XANES laboratory X-ray spectrometer at University of Washington," J. Synch. Rad. vol. 26, eight pages, (2019).

Huang et al., "Theoretical analysis and optimization of highly efficient multilayer-coated blazed gratings with high fix-focus constant for the tender X-ray region," Op. Express Vo. 28, No. 2, pp. 821-845 (2020).

(56) References Cited

OTHER PUBLICATIONS

Kim et al., "A Simulation Study on the Transfer Characteristics of the Talbot Pattern Through Scintillation Screens in the Grating Interferometer," J. Rad. Sci. and Tech. 42(1), pp. 67-75 (2019).
Kulow et al., "On the Way to Full-Field X-ray Fluorescence Spectroscopy Imaging with Coded Apertures," J. Anal. At. Spectrom. Doi: 10.1039/C9JA00232D (2019).
Li et al., "Production and Heat Properties of an X-ray Reflective Anode Based on a Diamond Heat Buffer Layer," Materials vol. 13, p. 241 (2020).
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Zhou et al., "Quasi-parallel X-ray microbeam obtained using a parabolic monocapillary X-ray lens with an embedded square-shaped lead occluder," arXiv:2001.04667 (2020).
"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.
"Element Six CVD Diamond Handbook" (Element Six, Luxembourg, 2015).
"High performance benchtop EDXRF spectrometer with Windows° software," published by: Rigaku Corp., Tokyo, Japan; 2017.
"Monochromatic Doubly Curved Crystal Optics," published by: X-Ray Optical Systems, Inc. (XOS), East Greenbush, NY; 2017.
"Optics and Detectors," Section 4 of X-Ray Data Booklet, 3rd Ed., A.C. Thompson ed. (Lawrence Berkeley Nat'l Lab, Berkeley, CA, 2009).
"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.
"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nat'l Lab, Berkeley, CA, Dec. 2008).
"Series 5000 Packaged X-ray Tubes," Product Technical Data Sheet DS006 Rev. G, X-Ray Technologies Inc. (Oxford Instruments), Scotts Valley, CA (no date).
"Toward Control of Matter: Energy Science Needs for a New Class of X-Ray Light Sources" (Lawrence Berkeley Nat'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published—2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition", (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Bachucki et al., "Laboratory-based double X-ray spectrometer for simultaneous X-ray emission and X-ray absorption studies," J. Anal. Atomic Spectr. DOI:10.1039/C9JA00159J (2019).
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article No. 03209.
Bech, "X-ray imaging with a grating interferometer," University of Copenhagen PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Chon, "Measurement of Roundness for an X-Ray Mono-Capillary Optic by Using Computed Tomography," J. Korean Phys. Soc. vol. 74, No. 9, pp. 901-906 (May 2019).
Coan et al., "In vivo x-ray phase contrast analyzer-based imaging for longitudinal osteoarthritis studies in guinea pigs," Phys. Med. Biol. vol. 55(24) (2010), pp. 7649-7662.

(56) References Cited

OTHER PUBLICATIONS

Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628-635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing,, Applications" (Springer Science + Business Media, New York, 2009).
Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.
Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Günther et al., "Full-field structured-illumination super-responution X-ray transmission microscopy," Nature Comm. 10:2494 (2019) and supplementary information.
Guttmann et al., "Ellipsoidal capillary as condenser for the BESSY full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.
Hennekam et al., "Trace metal analysis of sediment cores using a novel X-ray fluorescence core scanning method," Quaternary Int'l, https://doi.org/10.1016/j.quaint.2018.10.018 (2018).
Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-RAY Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jahrman et al., "Vacuum formed temporary spherically and toroidally bent crystal analyzers for x-ray absorption and x-ray emission spectroscopy," Rev. Sci. Inst. vol. 90, 013106 (2019).
Jiang et al., "X-Ray Phase-Contrast Imaging with Three 2D Gratings," Int. J. Biomed. Imaging, (2008), 827152, 8 pages.
Jin et al., "Development of an X-ray tube with two selective targets modulated by a magnetic field," Rev. Sci. Inst. vol. 90, 083105 (2019).
Joy, "Astronomical X-ray Optics," Ch. 28 of "Handbook of Optics vol. III, 2nd Ed.," (McGraw Hill, New York, 2001).

(56) References Cited

OTHER PUBLICATIONS

Kalasová et al., "Characterization of a laboratory-based X-ray computed nonotomography system for propagation-based method of phase contrast imaging," IEEE Trans. On Instr. And Meas., DOI 10.1109/TIM.2019.2910338 (2019).

Keyrilainen et al., "Phase contrast X-ray imaging of breast," Acta Radiologica, vol. 51 (8), (2010), pp. 866-884. Jan. 18, 2010 pub Jun. 15, 2010.

Kidalov et al., "Thermal Conductivity of Diamond Composites," Materials, vol. 2 (2009) pp. 2467-2495.

Kido et al., "Bone Cartilage Imaging with X-ray Interferometry using a Practical X-ray Tube", in Medical Imaging 2010: Physics of Medical Imaging, Proc. SPIE vol. 7622 (2010), 762240.

Kim, "Talbot images of wavelength-scale amplitude gratings," Opt. Express vol. 20(5), (2012), pp. 4904-4920.

Kim et al., "Observation of the Talbot Effect at Beamline 6C Bio Medical Imaging of he Pohang Light Source-II," J. Korean Phys. Soc., vol. 74, No. 10, pp. 935-940 (May 2019).

Kirkpatrick et al., "Formation of Optical Images by X-Rays", J. Opt. Soc. Am. vol. 38(9) (1948), pp. 766-774.

Kirz, "Phase zone plates for x rays and the extreme uv," J. Op. Soc. Am. vol. 64 (Mar. 1974), pp. 301-309.

Kirz et al., "The History and Future of X-ray Microscopy", J. Physics: Conden. Series vol. 186 (2009): 012001.

Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.

Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).

Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).

Kottler et al., "A two-directional approach for grating based differential phase contrast imaging using hard x-rays," Opt. Express vol. 15(3), (2007), pp. 1175-1181.

Kottler et al., "Dual energy phase contrast x-ray imaging with Talbot-Lau interferometer," J. Appl. Phys. vol. 108(11), (2010), 114906. Jul. 7, 2010 pub Dec. 7, 2010.

Kumakhov et al., "Multiple reflection from surface X-ray optics," Physics Reports, vol. 191(5), (1990), pp. 289-350.

Kumakhov, "X-ray Capillary Optics. History of Development and Present Status" in Kumakhov Optics and Application, Proc. SPIE 4155 (2000), pp. 2-12.

Kuwabara et al., "Hard-X-ray Phase-Difference Microscopy with a Low-Brilliance Laboratory X-ray Source", Appl. Phys. Express vol. 4 (2011) 062502.

Kuznetsov, "X-Ray Optics Calculator," Institute of Microelectronics Technology and High Purity Materials, Russian Academy of Sciences (IMT RAS), Chernogolovka, Russia (6 pages submitted); 2016.

Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.

Lai, "X-Ray Microfocusing Optics," Slide Presentation from Argonne National Laboratory, 71 slides, Cheiron Summer School 2007.

Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.

Lechner et al., "Silicon drift detectors for high count rate X-ray spectroscopy at room temperature," Nuclear Instruments and Methods, vol. 458A (2001), pp. 281-287.

Leenaers et al., "Application of Glancing Incidence X-ray Analysis," 1997, X-ray Spectrometry, vol. 26, pp. 115-121.

Lengeler et al., "Refractive X-ray Optics," Ch. 20 of "Handbook of Optics vol. III, 2nd Ed." (McGraw Hill, New York, 2001.

Li et al., "Source-optic-crystal optimisation for compact monochromatic imaging," Proc. SPIE 5537 (2004), pp. 105-114.

Li et al., "X-ray phase-contrast imaging using cascade Talbot-Lau interferometers," Proc. SPIE 10964 (2018), pp. 1096469-1-1096469-6.

Li et al., "Study on High Thermal Conductivity of X-ray Anode with Composite Diamond Substrate,"—J. Phys.: Conf. Ser., vol. 1300, 012115 (2019).

Lohmann et al., "An interferometer based on the Talbot effect," Optics Communications vol. 2 (1971), pp. 413-415.

Lübcke et al., "Soft X-ray nanoscale imaging using a sub-pixel resolution charge coupled device (CCD) camera," Ref. Sci. Instrum. vol. 90, 043111 (2019).

Lühl et al., "Scanning transmission X-ray microscopy with efficient X-ray fluorescence detection (STXM-XRF) for biomedical applications in the soft and tender energy range," J. Synch. Rad. vol. 26, https://doi.org/10.1107/S1600577518016879, (2019).

Macdonald et al., "An Introduction to X-ray and Neutron Optics," Ch. 19 of "Handbook of Optics vol. III, 2nd Ed." (McGraw Hill, New York, 2001).

Macdonald et al., "Polycapillary and Multichannel Plate X-Ray Optics," Ch. 30 of "Handbook of Optics vol. III, 2nd Ed.," (McGraw Hill, New York, 2001).

Macdonald et al., "Polycapillary X-ray Optics for Microdiffraction," J. Appl. Cryst., vol. 32 (1999) pp. 160-167.

Macdonald, "Focusing Polycapillary Optics and Their Applications," X-Ray Optics and Instrumentation, vol. 2010, (Oct. 2010): 867049.

Maj et al., "Etching methods for improving surface imperfections of diamonds used for x-ray monochromators," Adv. X-ray Anal., vol. 48 (2005), pp. 176-182.

Malgrange, "X-ray Optics for Synchrotron Radiation," ACTA Physica Polonica A, vol. 82(1) (1992) pp. 13-32.

Malzer et al., "A laboratory spectrometer for high throughput X-ray emission spectroscopy in catalysis research," Rev. Sci. Inst. 89, 113111 (2018).

Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.

Matsushita, "Mirrors and Multilayers," Slide Presentation from Photon Factor, Tsukuba, Japan, 65 slides, (Cheiron School 2009, Sprint-8, Japan, Nov. 2009).

Matsushita, "X-ray monochromators," Slide Presentation from Photon Factory, Tsukuba, Japan, 70 slides, (Cheiron School 2009, Spring-8, Japan, Nov. 2009).

Matsuyama et al., "Wavefront measurement for a hard-X-ray nanobeam using single-grating interferometry", Opt Express vol. 20 (2012), pp. 24977-24986.

Miao et al., "Motionless phase stepping in X-ray phase contrast imaging with a compact source," Proceedings of the National Academy of Sciences, vol. 110(48), (2013), pp. 19268-19272.

Michette, "Zone and Phase Plates, Bragg-Fresnel Optics," Ch. 23 of "Handbook of Optics vol. III, 2nd Ed.," (McGraw Hill, New York, 2001).

Mizutani et al., X-ray microscopy for neural circuit reconstruction in 9th International Conference on X-Ray Microscopy, J. Phys: Conf. Ser. 186 (2009) 012092.

Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.

Momose et al., "Biomedical Imaging by Talbot-Type X-Ray Phase Tomography" in Developments in X-Ray Tomography V, Proc. SPIE vol. 6318 (2006) 63180T.

Momose et al., "Grating-Based X-ray Phase Imaging Using Multiline X-ray Source", Jpn. J. Appl. Phys. vol. 48 (2009), 076512.

Momose et al., "Phase Tomography by X-ray Talbot Interferometry for Biological Imaging" Jpn. J. Appl. Phys. vol. 45 2006 pp. 5254-5262.

Momose et al., "Phase Tomography Using X-ray Talbot Interferometer", in Synchrotron Radiation Instrumentation: Ninth International Conference, AIP Conf. Proc. vol. 879 (2007), pp. 1365-1368.

Momose et al., "Phase-Contrast X-Ray Imaging Using an X-Ray Interferometer for Biological Imaging", Analytical Sciences vol. 17 Supplement (2001), pp. i527-i530.

(56) References Cited

OTHER PUBLICATIONS

Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.
Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., "X-ray phase contrast imaging by compact Talbot-Lau interferometer with a signal transmission grating," 2014, Optics Letters, vol. 39, No. 15, pp. 4297-4300.
Morimoto et al., "Design and demonstration of phase gratings for 2D single grating interferometer," Optics Express vol. 23, No. 23, 29399 (2015).
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.

Noda et al., "Fabrication of High Aspect Ratio X-ray Grating Using X-ray Lithography" J. Solid Mech_ Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.
Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source', Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
Paxscan Flat Panel X-ray Imaging, Varian Sales Brochure, (Varian Medical Systems, Palo Alto, CA, Nov. 11, 2004).
Pfeiffer et al., "Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Reticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Pushie et al., "Elemental and Chemically Specific X-ray Fluorescence Imaging of Biological Systems," Chem. Rev. 114:17, 8499-8541 (2014).
Pushie et al., "Prion protein expression level alters regional copper, iron and zinc content in the mouse brain," Metallomics vol. 3, 206-214 (2011).
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Rix et al., "Super-Resolution X-ray phase-contrast and dark-field imaging with a single 2D grating and electromagnetic source stepping," Phys. Med. Biol. In press https://doi.org/10.1088/1361-6560/ab2ff5 (2019).

(56) References Cited

OTHER PUBLICATIONS

Röntgen, Ueber eine neue Art von Strahlen (Wurzburg Verlag, Wurzburg, Germany, 1896) also, in English, "On a New Kind of Rays," Nature vol. 53 (Jan. 23, 1896). pp. 274-276.
Rovezzi, "Study of the local order around magnetic impurities in semiconductors for spintronics." PhD Dissertation, Condensed Matter, Université Joseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS ONE, vol. 9, Issue 5 (May 2014) e93502.
Scholz, "X-ray Tubes and Monochromators," Technical Workshop EPIC, Universität Wurzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germany, 2006), pp. 85-198.
Scordo et al., "Pyrolitic Graphite Mosaic Drystal Thickness and Mosaicity Optimization for an Extended Source Von Hamos X-ray Spectrometer," Condens. Matter Vo. 4, pp. 38-52 (2019).
Scott, "Hybrid Semiconductor Detectors for High Spatial Resolution Phase-contrast X-ray Imaging," Thesis, University of Waterloo, Department of Electrical and Computer Engineering, 2019.
Sebert, "Flat-panel detectors:how much better are they?" Pediatr. Radiol. vol. 36 (Suppl 2), (2006), pp. 173-181.
Seifert et al., "Talbot-Lau x-ray phase-contrast setup for fast scanning of large samples," Sci. Rep. 9:4199, pp. 1-11 (2019).
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.
Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub 2011-12-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Strüder et al., "X-Ray Detectors," Ch. 4 of "X-ray Spectrometry: Recent Technological Advances," K. Tsuji et al. eds. (John Wiley & Sons, Ltd. Chichester, West Sussex, UK, 2004), pp. 63-131.
Stupple et al., "Modeling of Heat Transfer in an Aluminum X-Ray Anode Employing a Chemical Vapor Deposited Diamond Heat Spreader," J. Heat Transfer, Vo. 140, 124501-1-5 (Dec. 2018).
Sun et al., "Combined optic system based on polycapillary X-ray optics and single-bounce monocapillary optics for focusing X-rays from a conventional laboratory X-ray source," Nucl. Inst. and Methods in Phys. Res. A 802 (2015) pp. 5-9.
Sun et al., "Numerical design of in-line X-ray phase-contrast imaging based on ellipsoidal single-bounce monocapillary," Nucl. Inst. and Methods in Phys. Res. A746 (2014) pp. 33-38.
Sunday et al., "X-ray Metrology for the Semiconductor Industry Tutorial," J. Res. Nat'l Inst. Stan. vol. 124: 124003 (2019); https://doi.org/10.6028/jres.124.003.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published—2004 with product release).
Takahama, "RADspeed safire Digital General Radiography System Equipped with New Direct-Conversion FPD," Medical Now, No. 62 (2007).
Takeda et al., "Differential Phase X-ray Imaging Microscopy with X-ray Talbot Interferometer" Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science No IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tang et al., "Micro-computed tomography (MICRO-CT): a novel approach for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Terzano et al., Recent advances in analysis of trace elements in environmental samples by X-ray based techniques (IUPAC Technical Report), Pure Appl. Chem. 2019.
Tkachuk et al., "High-resolution x-ray tomography using laboratory sources", in Developments in X-Ray Tomography V, Proc. SPIE 6318 (2006): 631810.
Tkachuk et al., "Multi-length scale x-ray tomography using laboratory and synchrotron sources", Microsc. Microanal. vol. 13 (Suppl. 2) (2007), pp. 1570-1571.
Töpperwien et al., "Multiscale x-ray phase-contrast tomography in a mouse model of transient focal cerebral ischemia," Biomed. Op. Express, vol. 10, No. 1, Jan. 2019, pp. 92-103.
Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Advances," John Wiley & Sons Ltd. Chichester, West Susses, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Viermetz et al., "High resolution laboratory grating-based X-ray phase-contrast CT," Scientific Reports 8:15884 (2018).
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot-Lau Interferometer", Jpn. J. Appl. Phys. vol. 47 (2008), pp. 7412-7414.
Wang et al., "Advantages of intermediate X-ray energies in Zernike phase contrast X-ray microscopy," Biotech. Adv., vol. 31 (2013) pp. 387-392.

(56) References Cited

OTHER PUBLICATIONS

Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWORLD2015.
Wang et al., "Precise patterning of diamond films for MEMS application" Journal of Materials Processing Technology vol. 127 (2002), pp. 230-233.
Wang et al., "Measuring the average slope error of a single-bounce ellopsoidal glass monocapillary X-ray condenser based on an X-ray source with an adjustable source size," Nucl. Inst. And Meth. A934, 36-40 (2019).
Wang et al., "High beam-current density of a 10-keV nano-focus X-ray source," Nucl. Inst. And Meth. A940, 475-478 (2019).
Wansleben et al., "Photon flux determination of a liquid-metal jet x-ray source by means of photon scattering," arXiv:1903.06024v1, Mar. 14, 2019.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wittry et al., "Properties of fixed-position Bragg diffractors for parallel detection of x-ray spectra," Rev. Sci. Instr. vol. 64, pp. 2195-2200 (1993).
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.
Yashiro et al., "Optimal Design of Transmission Grating for X-ray Talbot Interferometer", Advances in X-ray Analysis vol. 49(3) (2006), pp. 375-379.
Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.
Yashiro et. al., "Hard-X-Ray Phase-Difference Microscopy Using a Fresnel Zone Plate and a Transmission Grating", Phys. Rev. Lett. vol. 103 (2009), 180801.
Yu et al., "Morphology and Microstructure of Tungsten Films by Magnetron Sputtering," Mat. Sci. Forum, vol. 913, pp. 416-423 (2018).
Zanette et al., "Two-Dimensional X-Ray Grating interferometer," Phys. Rev. Lett. vol. 105 (2010) pp. 248102-1 248102-4.
Zeeshan et al., "In-house setup for laboratory-based x-ray absorption fine structure spectroscopy measurements," Rev. Sci. Inst. 90, 073105 (2019).
Zeng et al., "Ellipsoidal and parabolic glass capillaries as condensers for x-ray microscopes," Appl. Opt. vol. 47 (May 2008), pp. 2376-2381.
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.
Zhang et al., "Application of confocal X-ray fluorescence based on capillary X-ray optics in nondestructively measuring the inner diameter of monocapillary optics," Optics Comm. (2018) https://doi.org/10.1016/j.optcom.2018.11.064.
Zhang et al., "Fabrication of Diamond Microstructures by Using Dry and Wet Etching Methods", Plasma Science and Technology vol. 15(6) (Jun. 2013), pp. 552-554.
Zhang et al., "Measurement of the inner diameter of monocapillary with confocal X-ray scattering technology based on capillary X-ray optics," Appl. Opt. (Jan. 8, 2019), doc ID 351489, pp. 1-10.

\* cited by examiner

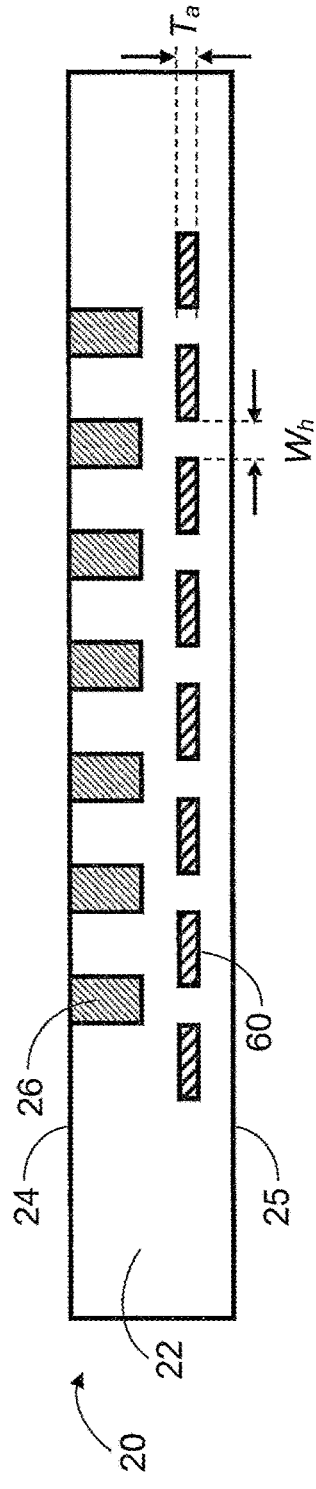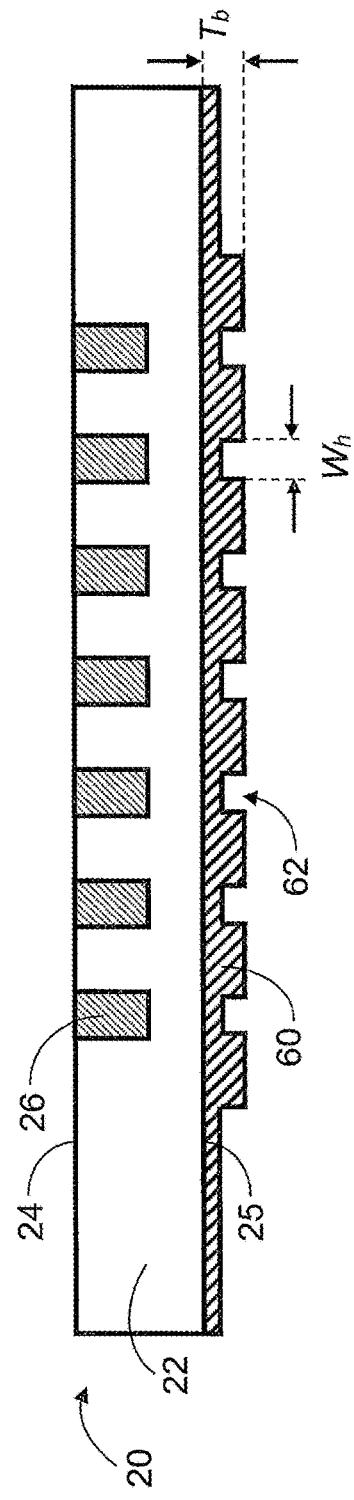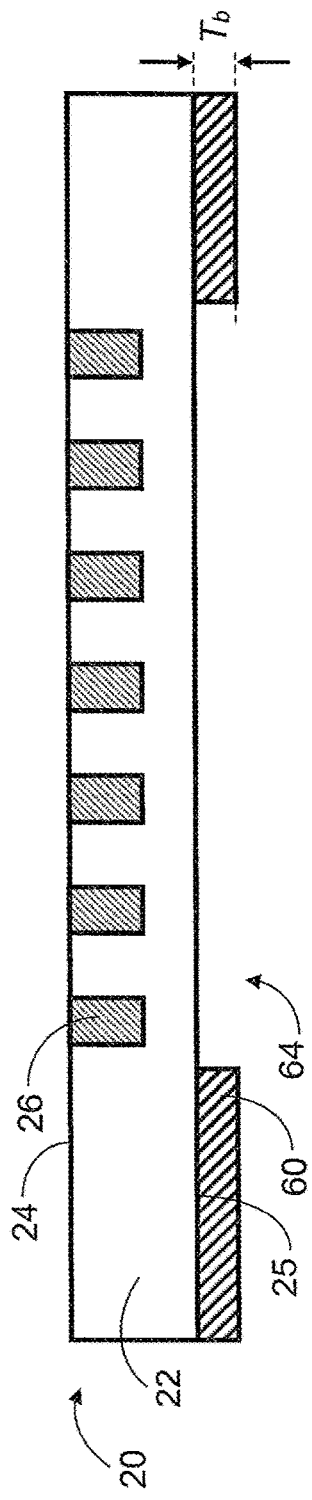

TALBOT-LAU X-RAY SOURCE AND INTERFEROMETRIC SYSTEM

CLAIM OF PRIORITY

The present application claims the benefit of priority to U.S. Provisional Appl. No. 62/715,164, filed Aug. 6, 2018 which is incorporated in its entirety by reference herein.

BACKGROUND

Field

This application relates generally to x-ray sources.

Description of the Related Art

Laboratory x-ray sources generally bombard a metal target with electrons, with the deceleration of these electrons producing Bremsstrahlung x-rays of all energies from zero to the kinetic energy of the electrons. In addition, the metal target produces x-rays by creating holes in the inner core electron orbitals of the target atoms, which are then filled by electrons of the target with binding energies that are lower than the inner core electron orbitals, with concomitant generation of x-rays with energies that are characteristic of the target atoms. Most of the power of the electrons irradiating the target is converted into heat (e.g., about 60%) and backscattered and/or reflected electrons (e.g., about 39%), with only about 1% of the incident power converted into x-rays. Melting of the x-ray target due to this heat can be a limiting factor for the ultimate brightness (e.g., photons per second per area per steradian) achievable by the x-ray source.

SUMMARY

Certain embodiments described herein provide an x-ray source comprising a target that comprises a substrate and a plurality of structures. The substrate comprises a thermally conductive first material and a first surface. The plurality of structures is on or embedded in at least a portion of the first surface. The structures are separate from one another and are in thermal communication with the substrate. The structures comprise at least one second material different from the first material, the at least one second material configured to generate x-rays upon irradiation by electrons having energies in an energy range of 0.5 keV to 160 keV. The x-ray source further comprises an electron source configured to generate the electrons and to direct the electrons to impinge the target and to irradiate at least some of the structures along a direction that is at a non-zero angle relative to a surface normal of the portion of the first surface. The angle and a kinetic energy of the electrons are configured such that at least some of the electrons have an electron penetration depth within the target sufficient to penetrate the first surface and irradiate at least two of the structures.

BRIEF DESCRIPTION OF THE DRAWINGS

FIGS. 2A-2C schematically illustrate example targets configured to improve the x-ray distribution from the target in accordance with certain embodiments described herein.

DETAILED DESCRIPTION

Certain embodiments described herein advantageously provide a micropatterned x-ray beam configured to be used in an imaging system utilizing a Talbot-Lau interferometry configuration (e.g., a Talbot x-ray microscope). Examples of such Talbot-Lau imaging systems include but are not limited to: medical imaging systems, such as radiography, tomosynthesis (e.g., for limited angle tomography to detect cancerous breast tissue), computed tomography (CT) (e.g., full tomographies), absorption-based x-ray microscopy in which the object's features of interest and a detector are placed within the same Talbot fringe, and x-ray dose-sensitive applications such as pediatric x-ray imaging and regularly scheduled mammographies; analysis of plastics and polymer blends (e.g., three-dimensional visualizations of polymer blend structures); imaging/tomography of interfaces between two or more materials having elements with low atomic numbers, such as implants (e.g., dermal fillers) in soft tissue and specimens that are in hydrated environments.

Various configurations of a Talbot-Lau imaging system which can utilize an x-ray source in accordance with certain embodiments described herein are disclosed in U.S. Pat. Nos. 9,719,947, 9,874,531, 10,349,908, and 10,352,880 and U.S. Pat. Appl. Publ. Nos. 2015/0117599A1 and 2016/0320320A1, each of which is incorporated herein in its entirety.

Figure 1A:
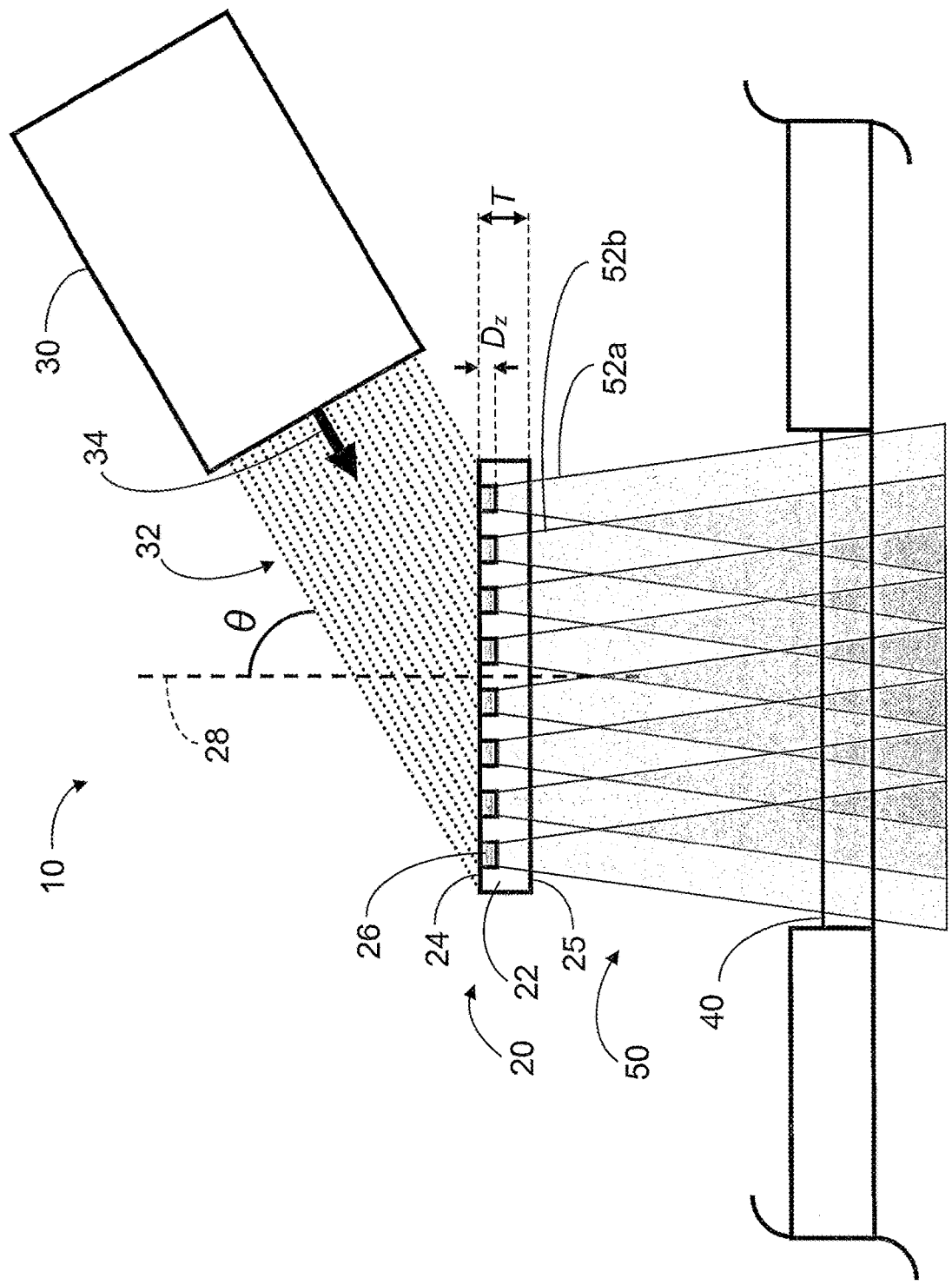
FIGS. 1A and 1B schematically illustrate cross-sectional views of a portion of an example x-ray source in accordance with certain embodiments described herein.
Figure 1B:
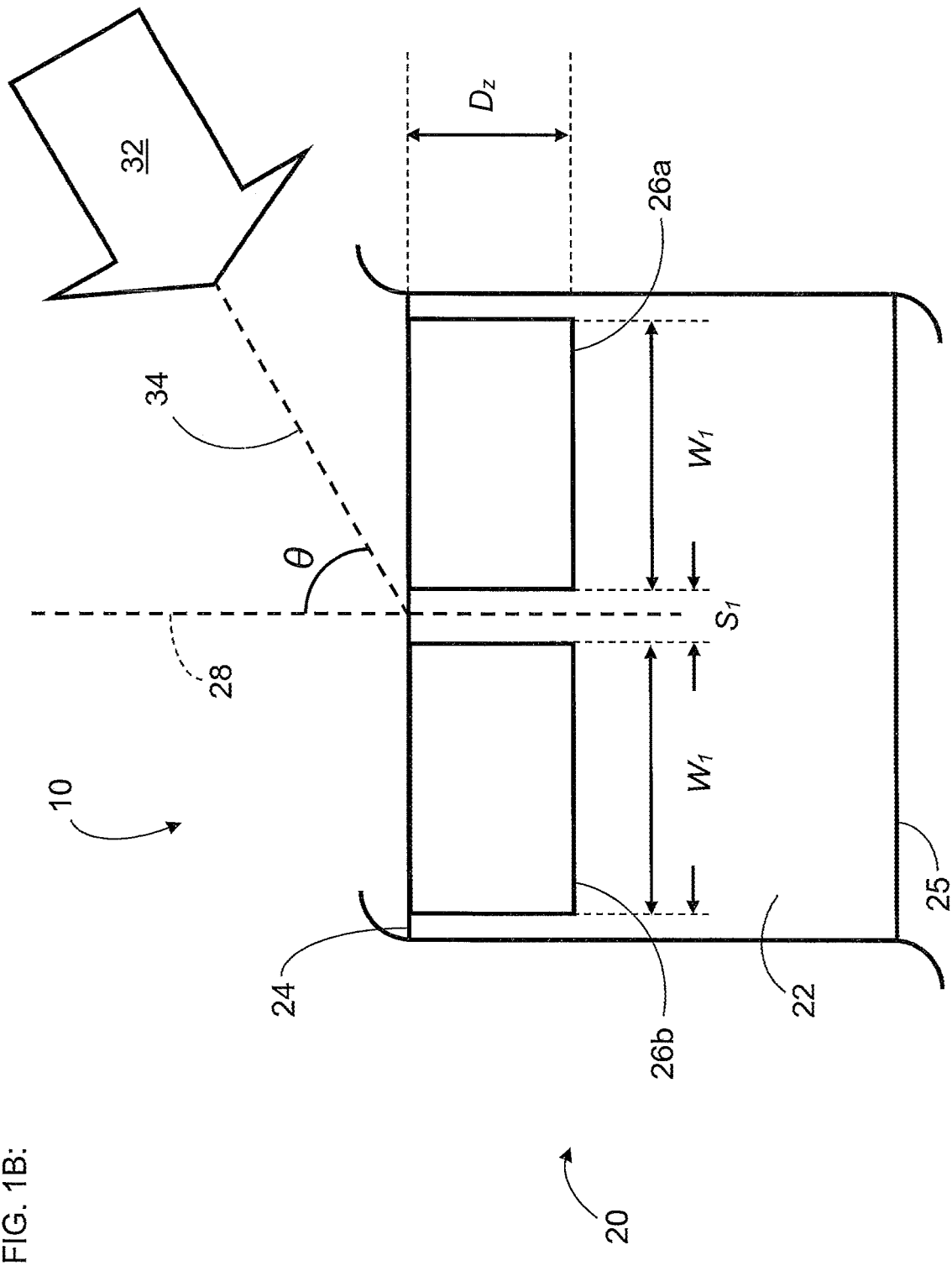

FIGS. 1A and 1B schematically illustrate cross-sectional views of a portion of an example x-ray source 10 in accordance with certain embodiments described herein. The source 10 comprises a target 20 and an electron source 30. The target 20 comprises a substrate 22 comprising a thermally conductive first material and a first surface 24. The substrate 22 further comprises a plurality of structures 26 on or embedded in at least a portion of the first surface 24. The structures 26 are separate from one another and in thermal communication with the substrate 22. The structures 26 comprise at least one second material different from the first material, and the at least one second material is configured to generate x-rays 50 upon irradiation by electrons 32 having energies in an energy range of 0.5 keV to 160 keV. The electron source 30 is configured to generate the electrons 32 and to direct the electrons 32 to impinge the target 20 and to irradiate at least some of the structures 26 along a first direction 34 that is at a non-zero angle relative to a surface normal 28 of the portion of the first surface 24. The angle and a kinetic energy of the electrons 32 are configured such that at least some of the electrons 32 have an electron penetration depth within the target 20 sufficient to penetrate the first surface 24 and irradiate at least two of the structures 26. In certain embodiments, the x-ray source 10 further comprises at least one optical element 40 (e.g., an x-ray window comprising the target 20). The at least one optical element 40 can be positioned such that at least some of the x-rays 50 are transmitted to or through the at least one optical element 40 (e.g., the at least some of the x-rays 50 are transmitted through the first material and to or through the at least one optical element 40).

Various configurations of a target 20, substrate 22, and plurality of structures 26 in accordance with certain embodiments described herein are disclosed in U.S. Pat. Nos. 9,719,947, 9,874,531, 10,349,908, and 10,352,880 and U.S. Pat. Appl. Publ. Nos. 2015/0117599A1 and 2016/0320320A1, each of which is incorporated herein in its entirety.

In certain embodiments, the substrate 22 comprises a body (e.g., wafer; plate, lamina) comprising the thermally conductive first material (e.g., having a thermal conductivity in: a range between 20 W/m-K and 2500 W/m-K; a range between 150 W/m-K and 2500 W/m-K; a range between 200 W/m-K and 2500 W/m-K; and/or a range between 2000 W/m-K and 2500 W/m-K) and comprises elements with atomic numbers less than or equal to 14. For example, the first material can comprise at least one of: diamond, beryllium, and sapphire. In certain other embodiments, the first material can comprise at least one of: copper, doped graphite, metal alloys, metal composite, graphite, diamond-like carbon, silicon, boron nitride, and silicon carbide. In certain embodiments, the body of the substrate 22 comprises a first surface 24 and a second surface 25, with the second surface 25 opposite to the first surface 24 (e.g., as schematically illustrated in FIGS. 1A and 1B). The second surface 25 of certain embodiments is generally parallel to the first surface 24 (e.g., as schematically illustrated in FIGS. 1A and 1B), while in certain other embodiments, the first surface 24 and the second surface 25 are non-parallel to one another. For example, the second surface 25 can be at a non-zero angle relative to the first surface 24, with the non-zero angle in a range greater than zero and less than 15 degrees or a range from 15 degrees to 45 degrees.

The substrate 22 of certain embodiments is planar and has a substantially flat first surface 24 and a substantially flat second surface 25 (e.g., as schematically illustrated in FIGS. 1A and 1B), while in certain other embodiments, the substrate 22 is non-planar and/or at least one of the first surface 24 and the second surface 25 is curved, stepped, or otherwise deviates from being flat. While FIGS. 1A and 1B schematically illustrate an example substrate 22 in which the surface normal 28 is uniform across the first surface 24 (e.g., different sub-portions of the first surface 24 have surface normals that are parallel to one another and point in the same direction as one another), the surface normal 28 can be non-uniform across the first surface 24 (e.g., different sub-portions of the first surface 24 have surface normals that are non-parallel and point in different directions as one another).

In certain embodiments, the substrate 22 has a thickness T (e.g., between the first surface 24 and the second surface 25) in a range of 100 microns to 250 microns, in a range of 250 microns to 3000 microns, in a range of 250 microns to 1000 microns, or in a range of less than 1000 microns. The thickness T of the substrate 22 of certain embodiments is uniform across the substrate 22, while in other certain embodiments, the thickness of the substrate 22 is different in different portions of the substrate 22.

In certain embodiments, the at least one second material of the structures 26 is selected to generate x-rays having a predetermined energy spectrum (e.g., x-ray intensity distribution as function of x-ray energy) upon irradiation by electrons having energies in the energy range of 0.5 keV to 160 keV. Examples of the at least one second material include but are not limited to, at least one of: tungsten, gold, molybdenum, chromium, copper, aluminum, rhodium, platinum, iridium, cobalt, tantalum, titanium, rhenium, silicon carbide, tantalum carbide, titanium carbide, boron carbide, and alloys or combinations including one or more thereof.

While FIGS. 1A and 1B schematically illustrate the structures 26 having a rectangular cross-sections with substantially straight sides, any other shape (e.g., regular; irregular; geometric; non-geometric) with straight, curved, and/or irregular sides is also compatible with certain embodiments described herein. In certain embodiments, the structures 26 extend from the first surface 24 towards the second surface 25 to a depth $D_z$ in a range of 1 micron to 30 microns, a range of 2 microns to 10 microns, a range of 3 microns to 7 microns, a range of 2 microns to 4 microns, or a range of less than 7 microns. In certain embodiments, the depth $D_z$ is selected based at least in part on the kinetic energy of the electrons 32, since the electron penetration depth is dependent on the electron kinetic energy and the material through which the electrons travel. For example, for structures 26 comprising gold, the depth $D_z$ can be selected to be in a range of 2 microns to 4 microns for 20 keV electrons, and to be in a range of 4 microns to 6 microns for 40 keV electrons.

While not shown in the cross-sectional views of FIGS. 1A and 1B, in certain embodiments, the structures 26 are arranged across a portion of the substrate 22 in a one-dimensional array (e.g., aligned with one another along a direction parallel to the first surface 24). For example, the structures 26 can comprise elongate strips or "lines" of the at least one second material that are spaced from one another and substantially parallel to one another (e.g., to be used in a one-dimensional Talbot-Lau imaging system). In certain other embodiments, the structures 26 are arranged across a portion of the substrate 22 in a two-dimensional array (e.g., aligned with one another along two directions perpendicular to one another and parallel to the first surface 24). For example, the structures 26 can comprise blocks, hexagonal (e.g., "honeycomb") prisms, or "dots" (e.g., cylinders) of the at least one second material that are spaced from one another in two lateral directions (e.g., to be used in a two-dimensional Talbot-Lau imaging system). In certain embodiments, the structures 26 are arranged in a mixture of one-dimensional and two-dimensional arrays.

In certain embodiments, at least some of the structures 26 each extend along the first surface 24 in at least one lateral direction (e.g., a direction parallel to the first surface 24) by a width W. For example, FIG. 1B shows structures 26 having a width $W_1$ and a separation distance $S_1$ between the structures 26 in a first lateral direction (e.g., a first direction parallel to the first surface 24; a first direction in a plane defined by the surface normal 28 and the direction 34 of electron irradiation). The width of the structures 26 in a second lateral direction perpendicular to the first lateral direction can be in a range of 0.5 micron to 10 millimeters; in a range of 0.5 micron to 5 millimeters; in a range of 0.5 micron to 1 millimeter; in a range of 0.2 millimeter to 3 millimeters. In certain embodiments (e.g., in which the structures 26 are arranged in a one-dimensional array or a two-dimensional array), the width $W_1$ of at least some of the structures 26 in the first lateral direction is in a range of 0.5 micron to 2 microns, in a range of 1 micron to 3 microns, in a range of 1 micron to 5 microns, or in a range of less than 5 microns, and the separation distance $S_1$ between at least some of the structures 26 in the first lateral direction is in a range of greater than 0.3 micron, in a range of 0.3 micron to 2 microns, in a range of 1 micron to 2 microns, or in a range of 1 micron to 4 microns. In certain embodiments, the duty cycle of the structures 26 (e.g., the ratio of the width W to the sum of the width W and the separation distance S, along a lateral direction of the first surface 24) is 33%, 50%, in a range of 20% to 40%, in a range of 40% to 60%, or in a range of 50% to 70%. In certain embodiments (e.g., in which the structures 26 are arranged in a two-dimensional array), the structures 26 also have a width $W_2$ and a separation distance $S_2$ between the structures 26 in a second lateral direction (e.g., a second direction parallel to the first surface 24; a second direction perpendicular to a plane defined by the surface normal 28 and the direction 34 of electron irradiation). In certain embodiments, the width $W_2$ of at least some of the structures 26 in the second lateral direction is in a range of 0.5 micron to 2 microns, in a range of 1 micron to 3 microns, in a range of 1 micron to 5 microns, or in a range of less than 5 microns, and the separation distance $S_2$ between at least some of the structures 26 in the second lateral direction is in a range of greater than 0.3 micron, in a range of 0.3 micron to 4 microns, or in a range of 1 micron to 2 microns. In certain embodiments (e.g., in which the structures 26 are arranged in linear-type array), the structures 26 have a width $W_2$ that is substantially larger than $W_1$, with the structures 26 arranged such that their widths $W_2$ are aligned with one another (e.g., forming a "dashed line" or "dotted line" array) or arranged such that the structures 26 are displaced, offset, or staggered relative to one another in a lateral direction perpendicular to their widths $W_2$. The separation distance $S_2$ between at least some of the structures 26 is in the range of 0.2 micron to 0.4 micron, 0.3 micron to 0.7 micron, or in a range of less than 2 microns. In certain embodiments, at least one of the separation distances $S_2$ is sufficiently large to facilitate (e.g., enhance; improve) thermal heat transfer from the structures 26 to the substrate 22 and from the substrate 22 to a heat sink in thermal communication with the substrate 22). In certain embodiments in which the electron penetration depths and/or the electron mean-free paths in the first and second materials as functions of the electron kinetic energy are known, the dimensions of the target 20 (e.g., one or more of the depth $D_z$, the width W, the separation distance S) and the electron propagation direction 34 are selected such that at least some of the electrons 32 propagate through two or more of the structures 26.

Specific embodiments of the design can vary depending on the intended application. For example, for mammography or for absorption-based, sub-micron resolution, 3D x-ray microscopy of semiconductor samples, the x-ray sources of certain embodiments can use electron accelerating voltages in a range of 20 keV to 70 keV. In certain such embodiments, the at least one second material of the structures 26 can be molybdenum, tungsten, and/or rhodium. Widths $W_1$ (and, if two-dimensional arrays, widths $W_2$) can be in the range of 0.3 micron to 1 micron, in a range of 0.5 micron to 1.5 microns, or in a range of 1 micron to 2 microns. The depths $D_2$ of the structures 26 can be selected to be less than half the continuous slowing down approximation (CSDA) estimate of the electron penetration depth of the electrons at their kinetic energy through the first material (e.g., diamond) and can be in a range of 1 micron to 3 microns, in a range of 2 microns to 5 microns, or in a range of 4 microns to 10 microns. For another example, x-ray microscopy and medical CT applications, the x-ray sources of certain embodiments can use higher electron accelerating voltages (e.g., up to 120 keV or up to 160 keV). In certain such embodiments, the at least one second material of the structures 26 can be tungsten. Widths $W_1$ (and, if two-dimensional arrays, $W_2$) can be in a range of 0.3 micron to 1 micron, in a range of 0.5 micron to 1.5 microns, or in a range of 1 micron to 3 microns. The depths $D_2$ of the structures 26 can be in a range of 2 microns to 5 microns, in a range of 4 microns to 8 microns, or in a range of 6 microns to 12 microns.

In certain embodiments, the target 20 further comprises at least one interface layer between the first material and the at least one second material, and the at least one interface layer comprises at least one third material different from the first material and the at least one second material. Examples of the at least one third material include but are not limited to, at least one of: titanium nitride (e.g., used with a first material comprising diamond and a second material comprising tungsten), iridium (e.g., used with a first material comprising diamond and a second material comprising molybdenum and/or tungsten), chromium (e.g., used with a first material comprising diamond and a second material comprising copper), beryllium (e.g., used with a first material comprising diamond), and hafnium oxide. In certain embodiments, the at least one interface layer has a thickness in a range of 1 nanometer to 5 nanometers, in a range of 2 nanometers to 30 nanometers, or in a range of 2 nanometers to 50 nanometers. In certain embodiments, the at least one third material is selected to provide a diffusion barrier layer configured to avoid (e.g., prevent; reduce; inhibit) diffusion of the at least one second material (e.g., tungsten) into the first material (e.g., diamond). For example, a diffusion barrier layer can be graded from a carbide material at an interface with the diamond first material to the at least one third material. In certain embodiments, the at least one third material is configured to enhance (e.g., improve; facilitate) adhesion between the at least one second material and the first material and/or to enhance (e.g., improve; facilitate) thermal conductivity between the at least one second material and the first material.

In certain embodiments, the target 20 further comprises at least one layer overlaying the structures 26 at the first surface 24. The at least one layer of certain embodiments comprises an electrically conductive material (e.g., doped diamond; nickel; aluminum) configured to be in electrical communication with electrical ground or another electrical potential to prevent charging of the first surface 24 due to electron irradiation of the target 20 and/or a sealing material (e.g., the first material; diamond; beryllium; sapphire) configured to seal the structures 26 between the at least one layer and the substrate 22.

In certain embodiments, the electron source 30 comprises an electron emitter having a dispenser cathode (e.g., impregnated tungsten), tungsten filament, lanthanum hexaboride ($LaB_6$) cathode, or carbon nanotubes configured to emit electrons 32 (e.g., via thermionic or field emission) to be directed to impinge the target 20. Example dispenser cathodes in accordance with certain embodiments described herein are marketed by Spectra-Mat, Inc. of Watsonville, Calif. (e.g., thermionic emitters comprising a porous tungsten matrix impregnated with barium aluminate).

The electron source 30 further comprises electron optics components (e.g., deflection electrodes; grids; electrostatic lens; magnetic lens; etc.) configured to deflect, shape, and/or focus the electrons 32 emitted from the electron emitter, to accelerate the electrons to a predetermined electron kinetic energy, and to direct the electrons 32 onto the target 10. Example configurations of electron optics components in accordance with certain embodiments described herein include but are not limited to, single-grid configurations, two-grid configurations, and three-grid configurations. In certain embodiments, the electron optics components are configured to limit where electrons are drawn from the electron emitter by setting up a retarding field, while other downstream electron optics components are used to draw electrons past the retarding field. In certain embodiments, the target 20 is configured to be used as an anode (e.g., set at a positive voltage relative to the electron source 30) to accelerate and/or otherwise modify the trajectories of the electrons 32. In certain embodiments, the target 20 is configured to be used as a grounded window to the source.

In certain embodiments, the electron source 30 is positioned relative to the target 20 such that the electrons 32 impinge the first surface 24 at a non-zero angle θ relative to a surface normal 28 of the portion of the first surface 24. For example, the angle θ can be greater than 20 degrees, in a range of 40 degrees to 85 degrees, in a range of 30 degrees to 70 degrees, or in a range of 40 degrees to 60 degrees. As schematically illustrated by FIGS. 1A and 1B, the angle θ is equal to 60 degrees. In certain embodiments in which the structures 26 are arranged in one or more one-dimensional (e.g., linear) arrays, the projection of the electron beam central line on the first surface 24 of the target 20 is parallel to a first lateral dimension (e.g., the shorter width $W_1$) and orthogonal to a second lateral dimension (e.g., the longer width $W_2$), to facilitate the electrons traveling through more than one structure 26. In certain embodiments in which the structures 26 are arranged in one or more two-dimensional arrays, the central electron beam projection can be diagonal to the array dimensions. In certain embodiments, the electrons 32 (e.g., in one or more electron beams) can be deflected and/or moved relative to the first surface 24 of the target 20 by one or more electromagnetic elements (e.g., one or more electrodes and/or one or more electromagnets) to irradiate different structured areas on the target 20. In certain other embodiments, the electrons 32 can be deflected and/or moved relative to the first surface 24 of the target 20 by mechanically moving one or more components of the electron source 30 (e.g., some or all of the electron source 30 being mounted on a mechanical flexure system). In certain embodiments, deflection and/or movement of the electrons 32 relative to the first surface 24 can modify the incident angle at which the electrons 32 irradiate the first surface 24, while in certain other embodiments, the incident angle is substantially unchanged by the deflection and/or movement of the electrons 32.

In certain embodiments, the electrons 32 impinging some of the structures 26 can be arranged in a single electron beam or in a plurality of electron beams, and the one or more electron beams can each have a rectangular-type beam profile, an oval-type beam profile, or another type of beam profile. In certain embodiments, at least some of the electrons 32 impinge different structures 26 at the same angle θ as one another (e.g., the electrons 32 are incident to each structure 26 of the plurality of structures 26 at substantially the same angle θ as one another, as schematically illustrated in FIG. 1A), while in certain other embodiments, at least some of the electrons 32 impinge different structures 26 at different non-zero angles θ as one another. In certain embodiments in which at least some of the structures 26 are separated from one another along a lateral direction of the target 20 (e.g., a direction parallel to the first surface 24), the electron source 30 is positioned relative to the target 20 such that a center line of the electrons 32 is in a plane defined by the surface normal 38 and the lateral direction (e.g., as schematically illustrated in FIG. 1A).

In certain embodiments, the kinetic energy of the electrons 32 impinging the structures 26 is in a range of 0.5 keV to 160 keV, in a range of 2 keV to 85 keV, in a range of 35 keV to 85 keV, in a range of 20 keV to 70 keV, in a range of 20 keV to 120 keV, in a range of 20 keV to 160 keV, or in any other range that is selected to provide x-rays with a predetermined energy spectrum. In certain embodiments, the angle θ and the electron kinetic energy are selected such that at least some of the electrons 32 have an electron penetration depth within the target 20 sufficient to penetrate the first surface 24 and irradiate at least two of the structures 26. In certain embodiments, the width W, the separation distance S, and the duty cycle (e.g., W/(W+S)) are selected to correspond to the incident electron beam energy and the angle θ, such that most electrons encounter more than one structure 26. In certain such embodiments, the dimensions W and S are sufficiently small that the electron penetration distance (e.g., average electron stopping distance), which is a function of both the material and the electron energy, extends at least through W/(sin θ) of the second material of the structures 26 (e.g., tungsten) and S/(sin θ) of the first material (e.g. diamond) at the predetermined electron accelerating voltage (e.g., the electron penetration distance is greater than (W+S)/(sin θ)). In certain embodiments, θ is 60 degrees.

For example, referring to FIG. 1B which schematically illustrates a first structure 26a and a second structure 26b separated from one another by a separation distance $S_1$ along a lateral direction of the first surface 24, the kinetic energy of the electrons 32 can be selected, using a continuous slowing down approximation (CSDA) estimate of the electron penetration depth, such that at least some of the electrons 32 propagate through the first structure 26a, through the portion of the substrate 22 between the first and second structures 26a, 26b, reaching the second structure 26b. In certain embodiments, the thickness T of the target 20 is configured to be less than the CSDA estimate of the electron penetration depth of the electrons 32 in the first material of the substrate 22, thereby avoiding (e.g., preventing; reducing; inhibiting) the contribution to the resultant x-rays from x-ray generation by deeper portions of the first material and/or the absorption by the first material of x-rays generated by the structures 26.

In certain embodiments, x-rays 50 are generated in each of the structures 26 irradiated by the electrons 32. As schematically illustrated in FIG. 1A, in certain embodiments, the x-rays 50 are emitted from the target 20 in a beam comprising a plurality of sub-beams 52a, 52b, . . . , each propagating from a corresponding one of the structures 26.

While FIG. 1A schematically illustrates the x-rays 50 as only being generated by and emitted from the structures 26, electron irradiation also produces x-ray generation from the substrate 22 (e.g., regions of the substrate 22 between the structures 26), and these x-rays generated within the substrate 22 can adversely degrade the resultant total x-ray distribution (e.g., reduce the discrimination of the structures 26 as separate x-ray emitters which is desired to facilitate use of the x-ray source 10 in a Talbot-Lau imaging system). For example, a desired x-ray spatial distribution (e.g., with the structures 26 serve as spatially distinct x-ray sub-sources) can be degraded by the substrate-generated x-rays, and a desired x-ray energy spectrum (e.g., with the x-rays having an intensity as a function of x-ray energy that is characteristic of the at least one second material of the structures 26) can be degraded by the x-rays generated by the first material.

FIGS. 2A-2C schematically illustrate example targets 20 configured to improve the x-ray distribution from the target 20 in accordance with certain embodiments described herein. As schematically illustrated in FIG. 2A, the target 20 comprises at least one layer 60 at a position between the structures 26 and the second surface 25 of the target 20. The at least one layer 60 comprises an x-ray absorbing material (e.g., gold) embedded within the substrate 22, having a thickness $T_a$ (e.g., in a range of 10 microns to 30 microns), and comprising holes directly below the structures 26 (e.g., having a pitch of 3 microns and lines of 2 microns). For example, the at least one layer 60 can be formed by depositing a uniform layer onto a back surface of the substrate 22, etching the layer 60 to form the desired microstructure, and then forming additional substrate material over the layer 60 on the back surface to form the second surface 25. Alternatively, a top portion of the substrate and a bottom portion of the substrate can be separately formed, the top portion having the structures 26 and the bottom portion with the at least one layer 60, and the two substrate portions can be joined together (e.g., adhered; clamped).

In certain embodiments, the at least one layer 60 effectively block many of the x-rays produced in the substrate 22 while allowing transmission of x-rays 50 produced in the structures 26. The at least one layer 60 has an aspect ratio defined by the thickness $T_a$ of the at least one layer 60 divided by the lateral width $W_h$ of the holes, and the aspect ratio of the at least one layer 60 can be lower than the aspect ratio of a conventional G0 absorption grid of a Talbot-Lau imaging system.

As schematically illustrated in FIG. 2B, the at least one layer 60 comprises an x-ray absorbing material (e.g., gold) deposited on the second surface 25, having a thickness $T_b$ (e.g., in a range of 10 microns to 60 microns), and comprising recesses 62 with a lateral width $W_h$ positioned directly below the structures 26 with a depth in a range of 3 microns to 100 microns). In certain embodiments, the at least one layer 60 also serves as a filter configured to reduce an energy bandwidth of the x-rays 50 (e.g., to filter the x-rays 50 to have a bandwidth of ±15% around an x-ray energy of interest). As schematically illustrated in FIG. 2C, the at least one layer 60 comprises an x-ray absorbing material (e.g., gold) deposited on the second surface 25, having a thickness $T_b$ (e.g., in a range of 10 microns to 60 microns), and comprising an aperture 64 with a lateral width sufficiently wide such that x-rays from a plurality of the structures 26 can propagate through the aperture 64. In certain such embodiments, the at least one layer 60 defines an outer boundary (e.g., perimeter) of an area through which the x-rays from the plurality of the structures 26 are emitted from the second surface 25 of the target 20.

In certain configurations, a target can comprise a thin layer of x-ray generating material (e.g., gold; tungsten; molybdenum) on a top surface of a substrate (e.g., diamond) and a plurality of structures on a bottom surface of the substrate which serve as an x-ray absorbing layer to define separate x-ray emitters.

Figure 1C:
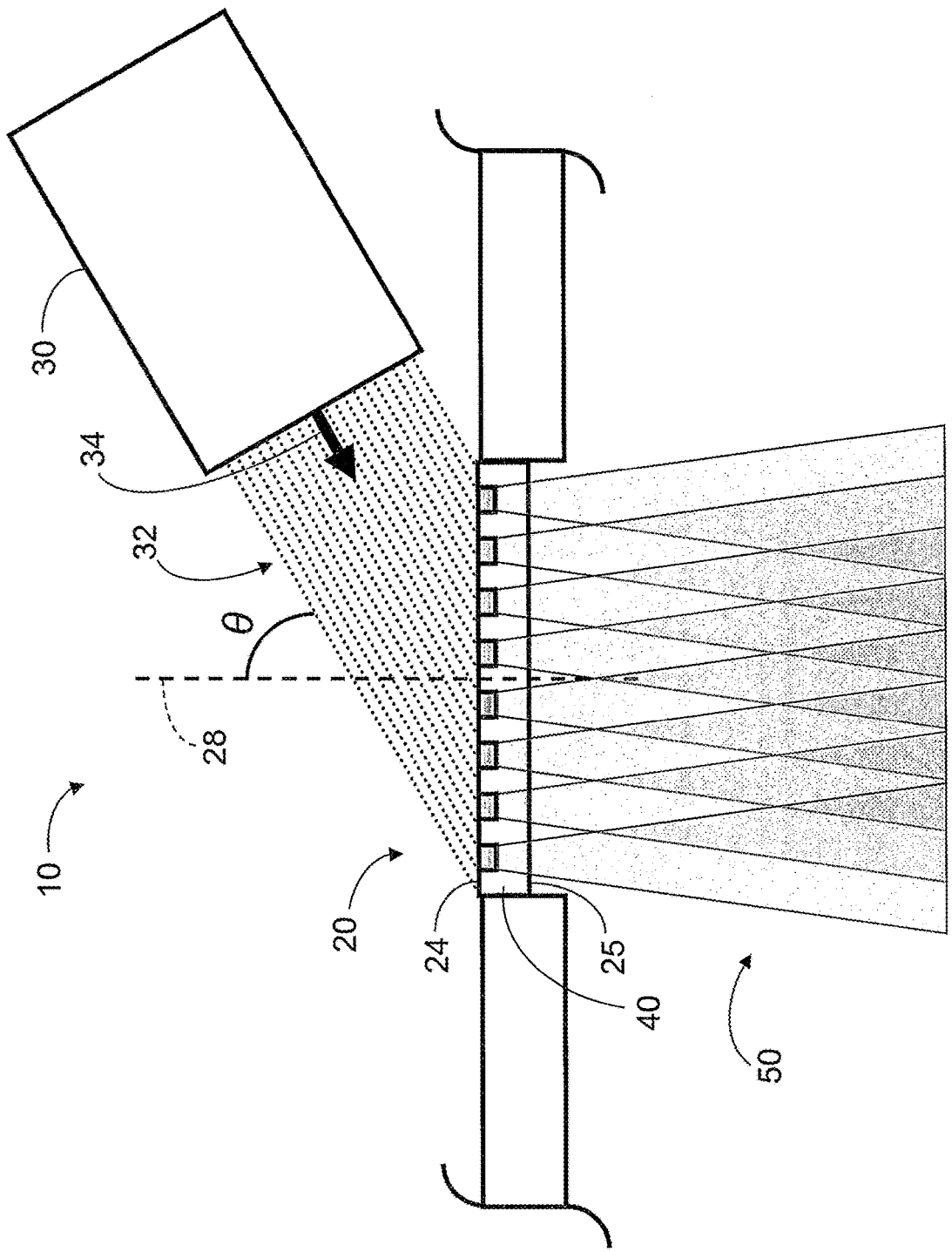
FIG. 1C schematically illustrates a cross-sectional view of a portion of an example x-ray source in which the at least one optical element comprises the target in accordance with certain embodiments described herein.

In certain embodiments, as schematically illustrated by FIG. 1A, the at least one optical element 40 is configured to receive at least some of the x-rays 50 emitted from the target 20. For example, the at least one optical element 40 comprises a window portion (e.g., a solid material that is substantially transparent to at least some of the x-rays 50 emitted from the target 20) of a housing wall of the x-ray source 10 and is spaced from the substrate 22 of the target 20. In certain embodiments, as schematically illustrated by FIG. 1C, the window portion comprises the target 20 (e.g., the housing wall of the x-ray source 10 comprises the substrate 22 such that the first surface 24 of the substrate 22 faces a region within the housing and the second surface 25 faces a region outside the housing). By having the window portion comprise the substrate 22, at least some of the x-rays transmitted through the first material are also transmitted through the window portion and are emitted from the target 20 (e.g., transmitted through the second surface 25). While FIG. 1C schematically illustrates only the edges of the substrate 22 being mechanically coupled to the housing of the x-ray source 10, in certain embodiments, the substrate 22 is mounted to a portion of the housing wall that is substantially transparent to at least some of the x-rays 50 emitted from the second surface 25 of the substrate 22. For example, the second surface 25 of the substrate 22 can be mounted to an inner surface of the portion of the housing wall.

For another example, the at least one optical element 40 comprises a grating (e.g., G1) of a Talbot-Lau imaging system and/or a sample being analyzed by the Talbot-Lau imaging system. For still another example, the at least one optical element 40 comprises an aperture and/or an x-ray optic configured to receive the x-rays 50 and to modify (e.g., focus; deflect; filter) the x-rays. Various optical elements in accordance with certain embodiments described herein are disclosed in U.S. Pat. Nos. 9,719,947, 9,874,531, 10,349,908, and 10,352,880 and U.S. Pat. Appl. Publ. Nos. 2015/0117599A1 and 2016/0320320A1, each of which is incorporated herein in its entirety.

In certain embodiments, the electron source 30 and the at least one optical element 40 are positioned at opposite side of the target 20 (e.g., the electron source 30 facing the first surface 24 and the at least one optical element 40 facing the second surface 25; see, e.g., FIG. 1A), which corresponds to a transmission x-ray source 10 configuration. In certain other embodiments, the electron source 30 and the at least one optical element 40 are positioned at the same side of the target 20 (e.g., the electron source 30 facing the first surface 24 and the at least one optical element 40 facing the first surface 24), which corresponds to a reflection x-ray source 10 configuration.

In certain embodiments, the incident angle θ of the electrons 32 to the first surface 24 is configured to advantageously increase the energy deposition in the structures 26 as compared to the energy deposition within the substrate 22. In certain such embodiments, the portion of the total energy deposition that is deposited in the structures 26 (e.g., the ratio of the energy deposition in the structures 26 with the total energy deposition) is increased by a factor (e.g., 2× to 5×).

Figure 3A:
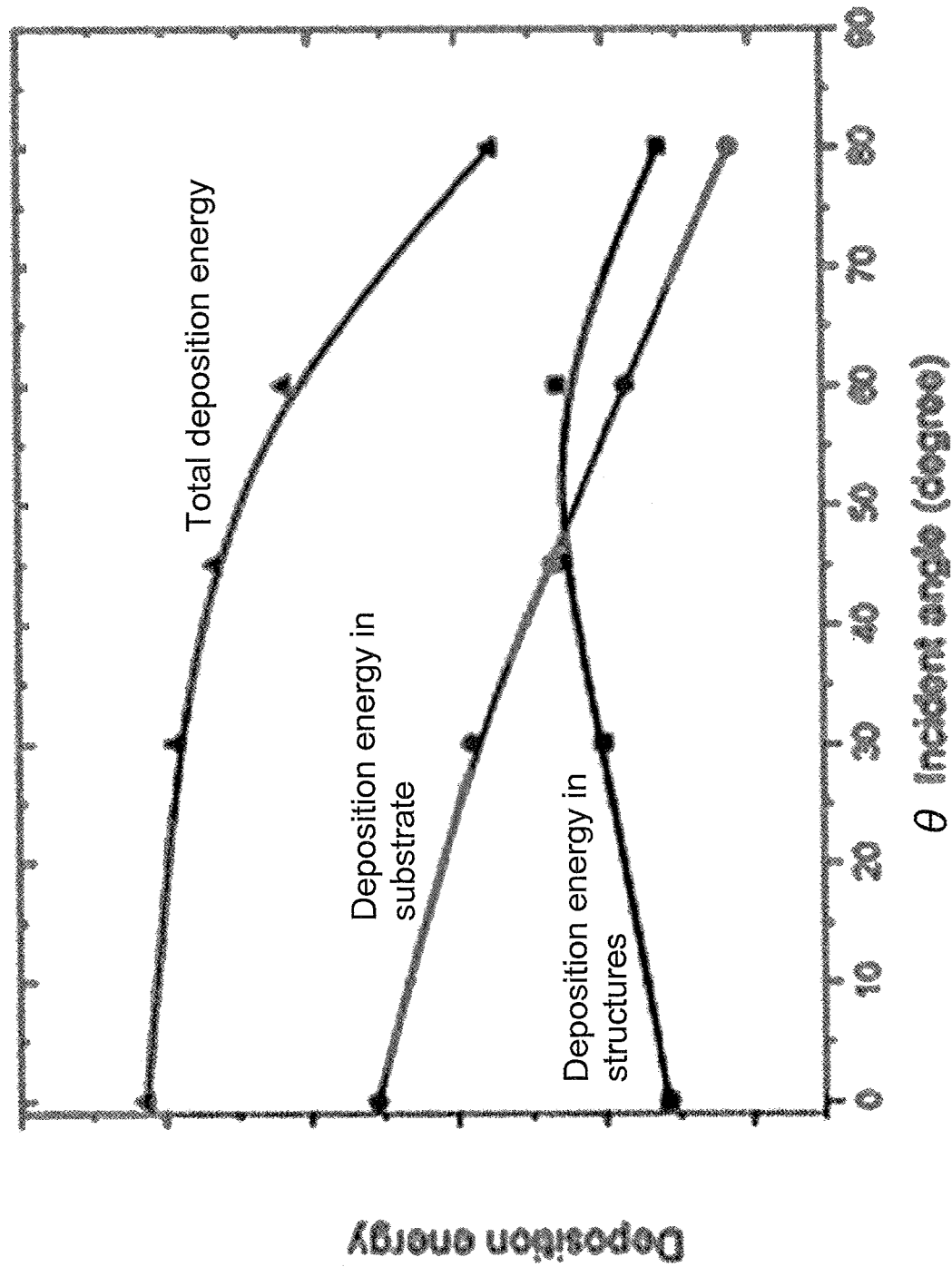
FIGS. 3A-3C show the results of simulation calculations for an electron beam of 30 keV impinging on a first surface of a target in accordance with certain embodiments described herein.
Figure 3C:
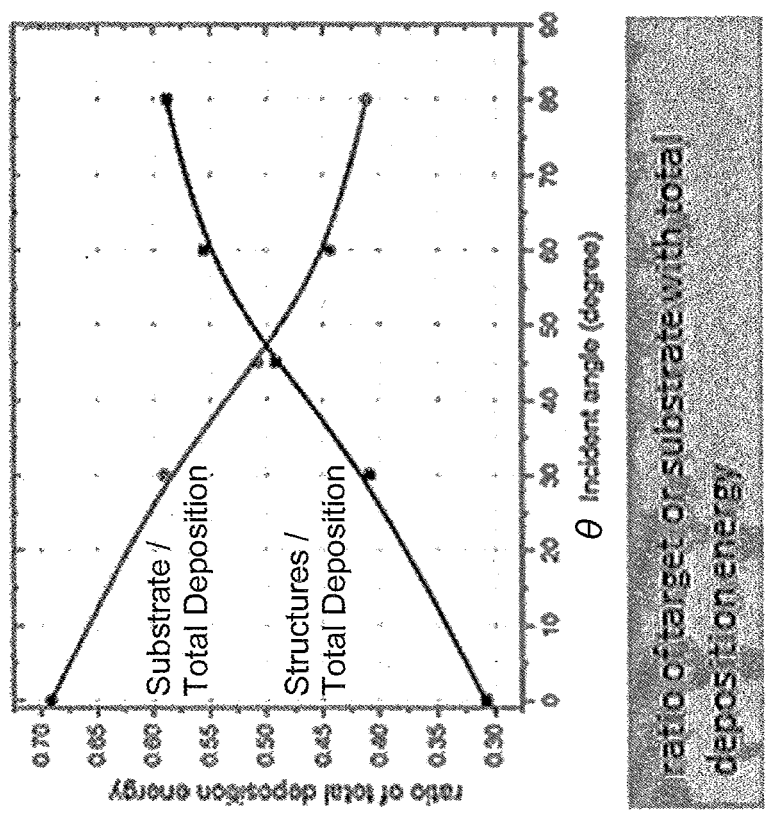
Figure 3B:
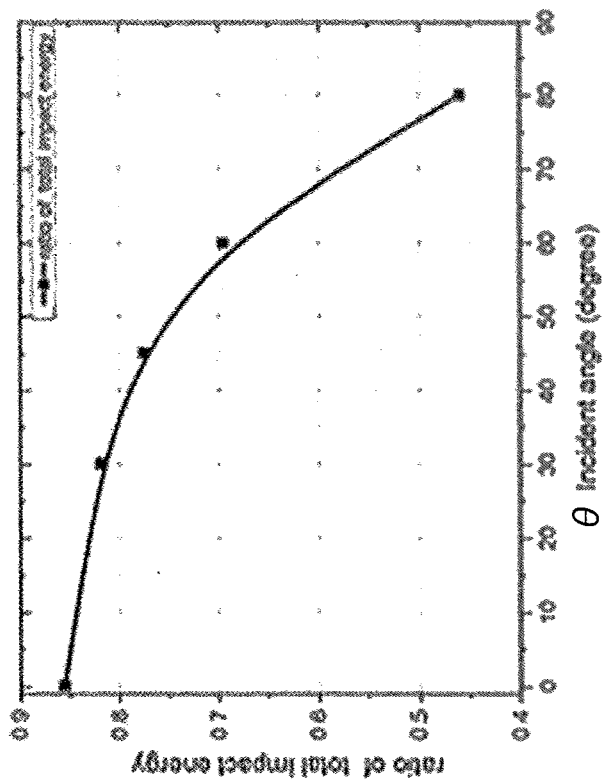

For example, FIGS. 3A-3C show the results of simulation calculations for an electron beam of 30 keV impinging on a first surface 24 of a target 20 in accordance with certain embodiments described herein. FIG. 3A shows a plot of the total deposition energy (in arbitrary units) from electrons impinging a first surface 24 of a target 20 as a function of incident angle θ (in degrees measured from the surface normal 28 of the first surface 24). At normal incidence (θ=0), the total deposition energy in the target 20 is at its largest, with about 15% of the energy lost to backscattered and/or reflected electrons. The total deposition energy in the target 20 monotonically becomes smaller with larger incidence angles due to increasing amounts of backscattered and/or reflected electrons which have an increasing fraction of the total impact energy incident on the target 20. FIG. 3B shows a plot of the ratio of the total deposition energy in the target 20 with the total impact energy incident on the target 20, which further illustrates this monotonic reduction of the total deposition energy with incident angle due to backscattered and/or reflected electrons. To account for backscattering of electrons at the higher incident angles, the electron loading power can be increased at higher angles.

Also, as shown in FIG. 3A, at normal incidence (θ=0), the deposition energy in the substrate 22 (i.e., the portion of the impact energy deposited in the substrate 22) is larger than the deposition energy in the structures 26 (i.e., the portion of the impact energy deposited in the structures 26). The deposition energy in the substrate 22 also decreases monotonically with larger incident angles, crossing the deposition energy in the structures 26 at an incident angle of about 53 degrees, while the deposition energy in the structures 26 has a maximum between 45 degrees and 60 degrees. At larger incident angles, the electrons 32 encounter more and more of the at least one second material of the structures 26, but with electrons 32 at incident angles above 20 degrees, the ratio of backscattered and/or reflected electrons increases significantly, resulting in a decrease of the total energy deposition and fewer electrons contributing to the x-ray generation.

FIG. 3C shows plots, as a function of incident angle, of (i) the ratio of the deposition energy in the substrate 22 with the total deposition energy, and (ii) the ratio of the deposition energy in the structures 26 with the total deposition energy. These two ratios are equal to one another at an incident angle of about 47 degrees, and at higher incident angles, the energy deposition to the structures 26 is greater than the energy deposition to the substrate 22. For example, at θ=60 degrees, energy deposited in the structures 26 is 55% of the total deposited energy while energy deposited in the substrate 22 is 45% of the total deposited energy. While more energy is lost to backscattered and/or reflected electrons at these higher incident angles (e.g., θ=60 degrees) as compared to normal incidence (see, FIG. 3B), by depositing a larger fraction of the total deposited energy in the structures 26 than in the substrate 22 (with a concomitant increase of the x-rays generated in the structures 26 and decrease of the x-rays generated in the substrate 22), certain embodiments advantageously provide higher contrast between x-ray emission from the structures 26 as compared to x-ray emission from the substrate 22 (e.g., portions between the structures 26), higher relative brightness of the x-ray emission from the structures 26 as compared to x-ray emission from the substrate 22 (e.g., portions between the structures 26), and/or improved Talbot fringe visibility.

In certain embodiments, the structural parameters of the target 20 (e.g., lateral size of the structures 26; pitch of the structures 26 across the first surface 24; distance between the structures 26; thickness of the structures 26) are selected to provide a desired trade-off between the increased interactions of the electrons 32 at higher incident angles and the decreased amount of x-ray generation due to backscattered and/or reflected electron losses. In certain embodiments, the electron kinetic energy is selected such that the average stopping range for the electrons 32 impinging the first surface 24 of the target 20 (e.g., including traveling through the first material and the second material) extends through more than one structure 26.

Various configurations have been described above. Although this invention has been described with reference to these specific configurations, the descriptions are intended to be illustrative of the invention and are not intended to be limiting. Various modifications and applications may occur to those skilled in the art without departing from the true spirit and scope of the invention. Thus, for example, in any method or process disclosed herein, the acts or operations making up the method/process may be performed in any suitable sequence and are not necessarily limited to any particular disclosed sequence. Features or elements from various embodiments and examples discussed above may be combined with one another to produce alternative configurations compatible with embodiments disclosed herein. Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

What is claimed is:

1. An x-ray source comprising:
   a target comprising:
      a substrate comprising a thermally conductive first material and a first surface; and
      a plurality of structures on or embedded in at least a portion of the first surface, the structures separate from one another and in thermal communication with the substrate, the structures comprising at least one second material different from the first material, the at least one second material configured to generate x-rays upon irradiation by electrons having energies in an energy range of 0.5 keV to 160 keV; and
   an electron source configured to generate the electrons and to direct the electrons to impinge the target and irradiate at least some of the structures along a direction that is at a non-zero angle relative to a surface normal of the portion of the first surface, the angle and a kinetic energy of the electrons configured such that at least some of the electrons have an electron penetration depth within the target sufficient to penetrate the first surface and irradiate at least two of the structures.

2. The x-ray source of claim 1, further comprising an x-ray window comprising the target, at least some of the x-rays transmitted through the first material and through a second surface of the target.

3. The x-ray source of claim 1, wherein the angle is greater than 20 degrees.

4. The x-ray source of claim 1, wherein the angle is in a range of 40 degrees to 85 degrees.

5. The x-ray source of claim 1, wherein the angle is in a range of 40 degrees to 60 degrees.

6. The x-ray source of claim 1, wherein the angle equals 60 degrees.

7. The x-ray source claim 1, wherein energy deposition from the electrons to the structures is greater than energy deposition from the electrons to the substrate.

8. The x-ray source of claim 1, wherein the substrate comprises a second surface that is opposite and generally parallel to the first surface, and the substrate has a thickness between the first surface and the second surface in a range of 250 microns to 3000 microns.

9. The x-ray source of claim 8, wherein the structures extend from the first surface towards the second surface to a depth in a range of 1 micron to 30 microns.

10. The x-ray source of claim 8, wherein the structures extend from the first surface towards the second surface to a depth in a range of 2 microns to 10 microns.

11. The x-ray source of claim 8, wherein the x-rays are transmitted through the second surface of the substrate to the at least one optical element.

12. The x-ray source of claim 1, wherein at least some of the structures each extend along the first surface in at least one lateral direction by a width in a range of 0.5 micron to 5 microns.

13. The x-ray source of claim 1, wherein at least some of the structures are separate from one another along the first surface by a separation distance greater than 0.3 micron.

14. The x-ray source of claim 13, wherein the separation distance is in a range of 1 micron to 2 microns.

15. The x-ray source of claim 1, wherein the first material comprises at least one of: diamond, silicon carbide, beryllium, and sapphire.

16. The x-ray source of claim 1, wherein the first material has a thermal conductivity in a range between 20 W/m-K and 2500 W/m-K and comprises elements with atomic numbers less than or equal to 14.

17. The x-ray source of claim 1, wherein the at least one second material comprises at least one of: tungsten, gold, and molybdenum.

18. The x-ray source of claim 1, wherein the target further comprises at least one interface layer between the first material and the at least one second material, the at least one interface layer comprising at least one third material different from the first material and the at least one second material.

19. The x-ray source of claim 18, wherein the at least one third material comprises at least one of: titanium nitride, iridium, and hafnium oxide.

20. The x-ray source of claim 1, wherein the target further comprises at least one layer overlaying the structures at the first surface.

21. The x-ray source of claim 20, wherein the at least one layer is electrically conductive and/or seals the structures between the at least one layer and the substrate.

22. The x-ray source of claim 20, wherein the at least one layer comprises the first material.

23. The x-ray source of claim 1, wherein the x-rays are in an energy range of 2 keV to 85 keV.

24. The x-ray source of claim 1, wherein the x-rays are emitted from the target in a beam comprising a plurality of sub-beams each propagating from a corresponding one of the plurality of structures.

25. The x-ray source of claim 1, further comprising at least one optical element positioned such that at least some of the x-rays are transmitted through the first material and to or through the at least one optical element, wherein the at least one optical element comprises a solid material that is substantially transparent to the at least some of the x-rays.

26. An x-ray interferometry system comprising:
an x-ray source comprising:
a target comprising:
a substrate comprising a thermally conductive first material and a first surface; and
a plurality of structures on or embedded in at least a portion of the first surface, the structures separate from one another and in thermal communication with the substrate, the structures comprising at least one second material different from the first material, the at least one second material configured to generate x-rays upon irradiation by electrons having energies in an energy range of 0.5 keV to 160 keV; and
an electron source configured to generate the electrons and to direct the electrons to impinge the target and irradiate at least some of the structures along a direction that is at a non-zero angle relative to a surface normal of the portion of the first surface, the angle and a kinetic energy of the electrons configured such that at least some of the electrons have an electron penetration depth within the target sufficient to penetrate the first surface and irradiate at least two of the structures.

27. The x-ray interferometry system of claim 26, having a Talbot-Lau interferometry configuration.

28. The x-ray interferometry system of claim 27, comprising a Talbot x-ray microscope.

\* \* \* \* \*

UNITED STATES PATENT AND TRADEMARK OFFICE
CERTIFICATE OF CORRECTION

PATENT NO. : 10,656,105 B2  
APPLICATION NO. : 16/525198  
DATED : May 19, 2020  
INVENTOR(S) : Yun et al.

Page 1 of 1

It is certified that error appears in the above-identified patent and that said Letters Patent is hereby corrected as shown below:

In the Specification

In Column 5, Line 28, delete "$S_2$" and insert --$S_1$, $S_2$--.

In Column 5, Line 51, delete "$D_2$" and insert --$D_z$--.

In Column 5, Line 65, delete "$D_2$" and insert --$D_z$--.

Signed and Sealed this  
Twenty-second Day of September, 2020

Andrei Iancu  
*Director of the United States Patent and Trademark Office*